US009782396B2

(12) United States Patent
Pettersson et al.

(10) Patent No.: US 9,782,396 B2
(45) Date of Patent: *Oct. 10, 2017

(54) ALFENTANIL COMPOSITION FOR THE TREATMENT OF ACUTE PAIN

(71) Applicant: Orexo AB, Uppsala (SE)

(72) Inventors: Anders Pettersson, Kode (SE); Barbro Johansson, Rönninge (SE); Emil Schwan, Uppsala (SE)

(73) Assignee: Orexo AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/138,570

(22) Filed: Apr. 26, 2016

(65) Prior Publication Data

US 2017/0071927 A1    Mar. 16, 2017

Related U.S. Application Data

(63) Continuation of application No. 14/331,507, filed on Jul. 15, 2014, now Pat. No. 9,345,698, which is a continuation of application No. 13/874,762, filed on May 1, 2013, now Pat. No. 8,815,911.

(30) Foreign Application Priority Data

May 2, 2012    (GB) .................................. 1207701.2
Nov. 23, 2012  (GB) .................................. 1221130.6

(51) Int. Cl.
| | |
|---|---|
| *A61K 31/445* | (2006.01) |
| *A61K 9/20* | (2006.01) |
| *A61K 31/454* | (2006.01) |
| *A61K 9/16* | (2006.01) |
| *A61K 9/00* | (2006.01) |

(52) U.S. Cl.
CPC ............ *A61K 31/454* (2013.01); *A61K 9/006* (2013.01); *A61K 9/0056* (2013.01); *A61K 9/1623* (2013.01); *A61K 9/2013* (2013.01); *A61K 9/2018* (2013.01); *A61K 9/2054* (2013.01); *A61K 9/2077* (2013.01)

(58) Field of Classification Search
CPC ............................ A61K 31/454; C07D 211/58
USPC .......................................... 514/329; 424/465
See application file for complete search history.

(56) References Cited

U.S. PATENT DOCUMENTS

| | | | |
|---|---|---|---|
| 5,785,989 A | 7/1998 | Stanley et al. | |
| 8,119,158 B2 | 2/2012 | Moe et al. | |
| 8,815,911 B2 * | 8/2014 | Pettersson | A61K 31/454 424/465 |
| 9,345,698 B2 * | 5/2016 | Pettersson | A61K 31/454 |
| 2002/0160043 A1 | 10/2002 | Coleman | |
| 2004/0180080 A1 | 9/2004 | Furusawa et al. | |
| 2005/0042281 A1 | 2/2005 | Singh et al. | |
| 2005/0142197 A1 | 6/2005 | Moe et al. | |
| 2005/0142198 A1 | 6/2005 | Moe et al. | |
| 2006/0281775 A1 | 12/2006 | Kelly et al. | |
| 2007/0036853 A1 | 2/2007 | Agarwal et al. | |
| 2007/0104763 A1 | 5/2007 | Jobdevairakkam et al. | |
| 2008/0268023 A1 | 10/2008 | Palmer et al. | |
| 2009/0011030 A1 | 1/2009 | Jouhikainen et al. | |
| 2009/0048237 A1 | 2/2009 | Palmer et al. | |
| 2009/0263476 A1 | 10/2009 | Jobdevairakkam et al. | |
| 2010/0015183 A1 | 1/2010 | Finn et al. | |
| 2010/0093712 A1 | 4/2010 | Kelley, II et al. | |
| 2010/0129443 A1 | 5/2010 | Pettersson | |
| 2010/0233257 A1 | 9/2010 | Herry et al. | |
| 2011/0071181 A1 | 3/2011 | Moe | |
| 2011/0091544 A1 | 4/2011 | Palmer | |
| 2011/0150989 A1 | 6/2011 | Park et al. | |
| 2012/0035216 A1 | 2/2012 | Palmer et al. | |

FOREIGN PATENT DOCUMENTS

| | | |
|---|---|---|
| EP | 1 115 383 A1 | 7/2001 |
| EP | 2 316 418 A2 | 5/2011 |
| WO | WO-91/03237 A1 | 3/1991 |
| WO | WO-99/24023 A2 | 5/1999 |
| WO | WO-00/16751 A1 | 3/2000 |
| WO | WO-00/51539 A1 | 9/2000 |
| WO | WO-01/30288 A1 | 5/2001 |
| WO | WO-02/067903 A2 | 9/2002 |
| WO | WO-03/005944 A1 | 1/2003 |
| WO | WO-2004/067004 A1 | 8/2004 |
| WO | WO-2006/097361 A1 | 9/2006 |
| WO | WO-2006/103418 A1 | 10/2006 |
| WO | WO-2007/081948 A2 | 7/2007 |

(Continued)

OTHER PUBLICATIONS

Extract from www.medicines.org.uk website RE: Rapifen®, Sep. 26, 2013.
*FDA Guidance for Industry: Orally Disintegrating Tablets*; Dec. 2008.
*JRS Pharma Technical Newsletter Issue* 2008, 1, 1-4.
Mohanachandran et al. *International Journal of Pharmaceutical Sciences Review and Research*, 6, 105 (2011).
Palm et al. *J. Pharmacol. Exp. Ther.*, 291, 435 (1999).

(Continued)

*Primary Examiner* — Raymond Henley, III
(74) *Attorney, Agent, or Firm* — Covington & Burling LLP

(57) ABSTRACT

There is provided pharmaceutical compositions for the treatment of pain e.g. short-term pain, which compositions comprise a mixture comprising:
(a) microparticles of alfentanil, or a pharmaceutically acceptable salt thereof, which microparticles are presented on the surfaces of larger carrier particles;
(b) a water-soluble weak base; and
(c) a compound which is a weak acid, which acid is presented in intimate mixture with the microparticles of alfentanil or salt thereof.

The composition may further comprise a disintegrant. The acid is preferably citric acid.

22 Claims, 2 Drawing Sheets

(56) References Cited

FOREIGN PATENT DOCUMENTS

| WO | WO-2007/081949 A2 | 7/2007 |
|---|---|---|
| WO | WO-2007/141328 A1 | 12/2007 |
| WO | WO-2008/068471 A1 | 6/2008 |
| WO | WO-2008/085765 A2 | 7/2008 |
| WO | WO-2008/106689 A2 | 9/2008 |
| WO | WO-2010/017111 A1 | 2/2010 |
| WO | WO-2010/027770 A1 | 3/2010 |
| WO | WO-2010/059504 A1 | 5/2010 |
| WO | WO-2010/132605 A1 | 11/2010 |
| WO | WO-2010/141505 A1 | 12/2010 |
| WO | WO-2011/017484 A2 | 2/2011 |
| WO | WO-2011/057199 A1 | 5/2011 |

OTHER PUBLICATIONS

*Pharmaceutical Dosage Forms: Tablets.* vol. 1, 2nd Edition, Lieberman et al (eds.), Marcel Dekker, New York and Basel (1989) p. 354-356.
Pharmaceutics The science of dosage form design, Aulton (eds) Churchill Livingstone (2000) pp. 312-314.
"*Remington: The Science and Practice of Pharmacy*", Gennaro (ed.), Philadelphia College of Pharmacy & Sciences, 19th edition (1995).
Rowe et al. *Handbook of Pharmaceutical Excipients*, 6th ed. (2009).
Vollhardt, *Organic Chemistry* (1987).
Wang et al. *Eur. J. Pharm. Sci.*, 39, 272 (2010).
Waterman et al. *Pharmaceutical Development and Technology*, 7, 1 (2002).

\* cited by examiner

ALFENTANIL COMPOSITION FOR THE TREATMENT OF ACUTE PAIN

This application is a continuation, and claims the benefit under 35 U.S.C. 120, of U.S. patent application Ser. No. 14/331,507, now U.S. Pat. No. 9,345,698, which is a continuation, and claims the benefit under 35 U.S.C. 120, of U.S. patent application Ser. No. 13/874,762, filed on May 1, 2013, now U.S. Pat. No. 8,815,911, which claims the benefit under 35 U.S.C. 119 of United Kingdom patent application serial no. 1207701.2 filed on May 2, 2012, and of United Kingdom patent application serial no. 1221130.6 filed on Nov. 23, 2012, the disclosures of which are each incorporated by reference herein in their entireties.

This invention relates to new pharmaceutical compositions comprising alfentanil that are useful in the treatment of pain, particularly acute, short-term pain associated with surgical, diagnostic and/or care-related procedures, and may be administered transmucosally and in particular sublingually.

Opioids are widely used in medicine as analgesics. Indeed, it is presently accepted that, in the palliation of moderate to severe pain, no more effective therapeutic agents exist.

Opioid agonist analgesics are used to treat moderate to severe, chronic cancer pain, often in combination with non-steroidal anti-inflammatory drugs (NSAIDs), as well as acute pain (e.g. during recovery from surgery and breakthrough pain). Further, their use is increasing in the management of chronic, non-malignant pain.

Additionally, invasive surgical and/or diagnostic procedures often give rise to short-lasting but nonetheless intense pain, which it is desirable to control if possible. Painful, invasive diagnostic procedures such as soft tissue biopsies are frequently performed, particularly on elderly patients. Painful therapeutic procedures such as orthopedic manipulations, fracture repositions, minor surgery and invasive endoarterial interventions are frequent events in the hospital setting. Additionally, routine care procedures such as wound dressing, bedside examinations, turning, transportation, mobilization and various imaging procedures are other examples where short-lasting, moderate to severe pain is frequently reported.

Such pain is self-evidently a problem in itself. If particularly intense, such pain, even if it is very short-lasting, can cause undesirable stress/trauma in patients. Furthermore, the fear/anticipation of such pain can in itself give rise to stress/anxiety in some patients in need of surgical and/or diagnostic procedures, and in some cases may even result on non-compliance (i.e. consent not being given for the procedure). A particularly problem exists in those patients with a low tolerance to pain, such as children.

Moreover, for many of the above-mentioned procedures, the quality of the intervention may depend upon effective pain management.

There is thus a presently unmet clinical need for useful and reliable, short-acting product that is of use to prevention of moderate to severe, yet short-lasting, pain that is associated with painful surgical, diagnostic and/or care-related procedures.

At present, short acting analgesics and/or local anaesthetics may be given to patients prior to such procedures, but such treatments are often highly inconvenient. In addition to the fact that such anaesthetics are typically given by injection (which may carry similar problems to those identified above), residual local or systemic drug can take several hours to wear off. Furthermore, current non-parenteral treatment alternatives suffer from lengthy onset times and durations of action far beyond the actual need, resulting in unnecessary side-effects.

International patent applications WO 00/16751, WO 2004/067004, WO 2006/103418 and WO 2008/068471 all disclose drug delivery systems for the treatment of existing pain by sublingual administration, applying an interactive mixture principle, in which the active ingredient in microparticulate form is adhered to the surfaces of larger carrier particles in the presence of a bioadhesive and/or mucoadhesive promoting agent.

Prior art documents, including international patent applications WO 03/005944, WO 02/067903, WO 2007/141328, WO 2010/132605, WO 01/30288 and US patent application US 2009/0263476 A1 employ pH modifying agents to promote dissolution and/or absorption of active ingredients.

European patent application EP 2114383, US patent applications US 2008/0268023, US 2009/0048237 and US 2011/0091544, and international patent applications WO 2007/081949 and WO 2008/085765 on the other hand relate to formulations comprising (specifically-stated) non-ordered mixtures of opioids, for example sufentanil, bioadhesive and stearic acid, which form a hydrogel in use (sublingual delivery). International patent application WO 2010/059504 relates to a sufentanil formulation comprising oxygen scavengers in packaging to minimise degradation. It stated in that document that the use of antioxidants, such as butylated hydroxytoluene (BHT) in solid sufentanil formulations do not stop degradation of the API.

Dissolvable lozenges, in which drug is embedded in a matrix, are disclosed in US patent application US 2002/0160043 and international patent application WO 91/03237. International patent application WO 2008/106689 and US patent application US 2009/0011030 disclose powders for inhalation, but also cross-reference the fentanyl lollipop Actiq®.

Layered tablets are disclosed in international patent application WO 2006/097361 and US patent application 2010/0233257. In WO 2006/097361, a single compacted core is made from mannitol and microcrystalline cellulose (and optionally other excipients). This core is then coated with active ingredient (such as an opioid) in a solution or suspension. A pH-modifying component may be added at this stage. Spray-coated formulations are also disclosed in US 2010/0233257. Compressible interactive mixtures are neither mentioned nor suggested in either of these documents.

pH dependent transport of cationic drugs has been studied (see e.g. Palm et al, *J. Pharmacol. Exp. Ther.*, 291, 435 (1999) and Wang et al, *Eur. J. Pharm. Sci.*, 39, 272 (2010)). US patent application 2007/0104763 discloses a lozenge for intraoral delivery comprising micronized fentanyl dispersed in a matrix comprising dextrose. US patent application 2009/0263476 refers to opioid-containing (e.g. fentanyl) buccal tablets in which a filler is employed, which is an alkaline metal oxide or hydroxide to improve transmucosal drug absorption. The use of, for example, magnesium oxide and magnesium hydroxide to give a higher pH is stated to enhance absorption without leading to instability of drug exhibited with other bases.

Stabilisation of drugs to oxidative degradation is discussed generally in the review article by Waterman et al, *Pharmaceutical Development and Technology*, 7, 1 (2002). US patent application 2011/0150989 also discloses specific stabilised morphinan-containing granules.

Effervescent opioid containing formulations are disclosed in inter alia US patent applications 2005/0142197, 2005/0142198, 2007/0036853 and 2011/0071181. International patent application WO 99/24023 discloses a sublingual tablet comprising an opioid, such morphine, mannitol and citric acid (in addition to sodium citrate).

Figure 1:
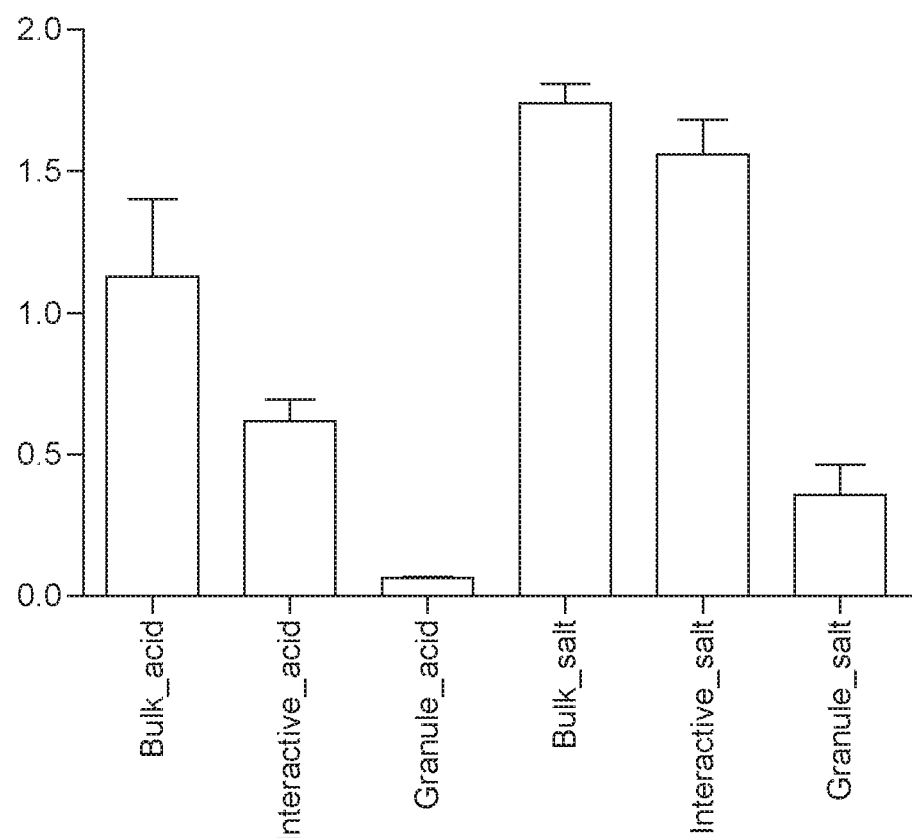
FIG. 1 shows a comparison of chemical stability of various batches of alfentanil-containing sublingual tablets.

There are currently no commercially-available solid state oral dosage formulations comprising the opioid analgesic alfentanil. It is instead administered intravenously as a sterile, non-pyrogenic, preservative free aqueous solution in a concentration of 500 μg alfentanil base per mL. The solution contains (as the only excipient) sodium chloride for isotonicity. To the applicant's knowledge, no short- or long-term stability issues have been reported for alfentanil solutions for injection.

We have surprisingly found that, when attempting to formulate alfentanil into a solid state, tablet formulation, a notable instability results. This instability is unexpectedly solved by the addition of a small amount of weak acid, such as citric acid, provided that that acid is presented in intimate mixture with the API.

Further, we have also found that a weak base, such as a sodium phosphate, may also be added to such formulations to enhance absorption and, even more surprisingly, that:
  (a) the presence of the weak base does not, as expected, have a detrimental effect on the stability of the alfentanil in such formulations; and
  (b) the enhanced absorption provided by the presence of the weak base is not, as expected, abrogated or cancelled out by the presence of the weak acid in such formulations.

According to a first aspect of the invention there is provided a pharmaceutical composition suitable for sublingual delivery which comprises a mixture comprising:
  (a) microparticles of alfentanil, or a pharmaceutically acceptable salt thereof, which microparticles are presented on the surfaces of larger carrier particles;
  (b) a water-soluble weak base, such as a phosphate; and
  (c) a compound which is a weak acid, which acid is presented in intimate mixture with the microparticles of alfentanil or salt thereof.

Such compositions are referred to hereinafter as "the compositions of the invention".

Alfentanil and pharmaceutically-acceptable salts thereof are presented in the compositions of the invention in the form of microparticles. Microparticles preferably possess a weight based mean diameter, number based mean diameter and/or a volume based mean diameter of between about 0.5 μm and about 30 μm, e.g. about 15 μm, such as between about 1 μm and about 10 μm. As used herein, the term "weight based mean diameter" will be understood by the skilled person to include that the average particle size is characterised and defined from a particle size distribution by weight, i.e. a distribution where the existing fraction (relative amount) in each size class is defined as the weight fraction, as obtained by e.g. sieving (e.g. wet sieving). As used herein, the term "number based mean diameter" will be understood by the skilled person to include that the average particle size is characterised and defined from a particle size distribution by number, i.e. a distribution where the existing fraction (relative amount) in each size class is defined as the number fraction, as measured by e.g. microscopy. As used herein, the term "volume based mean diameter" will be understood by the skilled person to include that the average particle size is characterised and defined from a particle size distribution by volume, i.e. a distribution where the existing fraction (relative amount) in each size class is defined as the volume fraction, as measured by e.g. laser diffraction.

Microparticles of active ingredient may be prepared by standard micronisation techniques, such as grinding, jet milling, dry milling, wet milling, precipitation, etc. An air elutriation process may be utilised subsequently to prepare specific size fractions, if required.

Preferred salts of alfentanil include hydrochloride salts.

Weakly acidic materials that may be mentioned include those that, when dissolved in water and/or saliva, enable the provision (at the site of administration of compositions of the invention) of a pH of between about 2.0 and about 6.5. For the purpose of this invention, the term includes substances that are safe for use in mammals, and includes weak acids, weak acid derivatives and other chemicals that convert to weak acids in vivo (e.g. precursors that convert to acids in vivo, by for example being sequentially activated in accordance with properties of the local environment). Typical pKas of weak acids are in the range of between about −1.5 (e.g. about −1.74) and about 16 (e.g. about 15.74) (e.g. see Vollhardt, *Organic Chemistry* (1987)). A preferred range is between about 1 and about 10. More preferably, the weakly acidic material comprises a weak acid that is safe for human consumption, for example a food acid, such as citric acid, tartaric acid, malic acid, fumaric acid, adipic acid, succinic acid, lactic acid, acetic acid, oxalic acid, maleic acid, ammonium chloride or a combination thereof. Preferred acids include tartaric acid and, particularly, citric acid.

Also useful in place of (and/or in addition to) weak acids are chelating agents or sequestering agents. The term "chelating" or "sequestering" agent may be defined as any ligand that is capable of coordinating to a metal through at least two interactions. Examples of such agents include adipic acid, succinic acid, lactic acid, oxalic acid, maleic acid, and salts of any of these or, more preferably, hydroxypropylbetadex, or acetic acid, pentetic acid, glutamic acid, citric acid, tartaric acid, fumaric acid, edetic acid, malic acid, or salts of any of these, including calcium acetate, disodium edentate and, particularly, sodium citrate.

Thus, compositions of the invention may in the alternative comprise:
  (a) microparticles of alfentanil, or a pharmaceutically acceptable salt thereof, which microparticles are presented on the surfaces of larger carrier particles;
  (b) a water-soluble weak base, such as a phosphate; and
  (c) a compound which is a sequestering agent, which agent is presented in intimate mixture with the microparticles of alfentanil or salt thereof.

In such instances, all preferred features of the invention as described herein for, and all statements and/or references made in respect of, weak acid materials may be applied equally to sequestering agents.

To provide compositions of the invention, microparticles of alfentanil or pharmaceutically-acceptable salts thereof are presented in intimate mixture with particles of weakly acidic material. By "intimate mixture" we mean that some form of mixing step (simple mixing, granulation or otherwise) takes place as between the alfentanil/salt microparticles and particles of weakly acidic material, rendering them in intimate contact with each other. In this respect, as employed herein, the terms "intimate mixture" and "intimate contact" may be employed interchangeably.

Compositions of the invention are presented in the form of a mixture comprising carrier particles upon the surfaces of which are presented (e.g. adhered) microparticles of alfentanil or a pharmaceutically acceptable salt thereof. Such a mixture may be termed an interactive mixture.

Carrier particles in interactive mixtures may comprise pharmaceutically-acceptable substances that are soluble in water, such as carbohydrates, e.g. sugars, such as lactose, and sugar alcohols, such as mannitol, sorbitol and xylitol; or pharmaceutically-acceptable inorganic salts, such as sodium chloride. Alternatively, carrier particles may comprise pharmaceutically-acceptable substances that are insoluble or sparingly soluble in water, such as dicalcium phosphate anhydrate, dicalcium phosphate dihydrate, tricalcium phosphate, calcium carbonate, and barium sulphate; starch and pre-gelatinised starch; bioadhesive and mucoadhesive materials, such as crosslinked polyvinylpyrrolidone and croscarmellose sodium; and other polymers, such as microcrystalline cellulose, cellulose; or mixtures thereof.

By "soluble in water" we include that the material has a solubility in water that is greater than 33.3 mg/mL at atmospheric pressure (e.g. 1 bar) and room temperature (e.g. 21° C.). On the other hand, the term "sparingly soluble or insoluble in water" includes materials that have a solubility in water that is less than 33.3 mg/mL under the same conditions. Preferred carrier particle materials include carbohydrates, including sugar alcohols, such as sorbitol, xylitol and, particularly, mannitol.

In order to provide intimate mixture/contact of microparticles of alfentanil or salt thereof and particles of weakly acidic material, the latter may be presented, for example either:

(a) within (i.e. as at least part of) said carrier particles, such that said carrier particles comprise or consist of said weak acid material, for example carrier particles may comprise a composite of weak acid material and another carrier particle material; and/or (b) upon the surfaces of the carrier particles, along with the microparticles of alfentanil or salt thereof (e.g. as part of an interactive mixture).

In this respect, any technique may be employed that involves forcing together weakly acidic material and carrier particles carrying microparticles of alfentanil or salt thereof, for example a compaction technique, such as compression and/or granulation.

Although weakly acidic material may also be presented between such carrier particles carrying the alfentanil/salt, we have found that it is important that at least some (e.g. about 10%, such as about 20%, for example about 30%, including about 40%, such as about 50%) of the weakly acidic material that is included in a composition of the invention is presented in intimate mixture with the alfentanil/salt, for example either as part of the interactive mixture, so that it is in contact with (e.g. adhered to) the surfaces of the carrier particles, and/or within said carrier particles, as described herein. We have found that, if weakly acidic material is only presented between such carrier particles carrying the alfentanil/salt (i.e. within the "bulk" along with the base), in the amounts mentioned herein, the stability advantages discussed herein are surprisingly not observed.

The term "interactive" mixture will be understood by those skilled in the art to include the term "ordered" mixture, and to denote a mixture in which particles do not appear as single units, as in random mixtures, but rather where smaller particles (e.g. microparticles of, for example, alfentanil) are attached to (i.e. adhered to or associated with) the surfaces of larger carrier particles. Such mixtures are characterised by interactive forces (for example van der Waals forces, electrostatic or Coulomb forces, and/or hydrogen bonding) between carrier and surface-associated particles (see, for example, Staniforth, *Powder Technol.*, 45, 75 (1985)). In final mixtures, and compositions comprising such mixtures, the interactive forces need to be strong enough to keep the adherent particles at the carrier surface.

When interactive mixtures are employed carrier particles may be of a size (weight and/or volume based average or mean diameter, vide supra) that is between about 30 µm and about 1000 µm (e.g. about 800 µm, such as about 750 µm), and preferably between about 50 (such as about 100 µm) and about 600 µm (such as about 500 µm, or about 450 µm), for example about 400 µm.

When employed in particulate form in intimate mixture with alfentanil or salt thereof on the surfaces of carrier particles, suitable particle sizes of weakly acidic materials that may be employed are in the ranges discussed hereinbefore for alfentanil or salt thereof.

Carrier particles comprising weakly acidic materials may comprise composites of such materials with other carrier particle materials and may be prepared by direct compression or granulation (wet or dry), for example as described hereinafter. In such instances, suitable particle sizes (weight and/or volume based average or mean diameter, vide supra) of weakly acidic materials that may be employed are higher than the ranges discussed hereinbefore and may be in the range of about 30 µm and about 400 µm), and preferably between about 40 µm (such as about 50 µm) and about 200 µm (such as about 150 µm or about 100 µm).

The skilled person will appreciate that, when weak acids are employed which are not solids (and therefore not particulate) at or around room temperature and atmospheric pressure, they may be adsorbed onto a particulate carrier material (such as silica) in order to provide particles comprising the weakly acidic material. Such may then be employed in intimate mixture with the alfentanil/salt or as part of a carrier composite.

Compositions of the invention further comprise a weak base, such as a water-soluble phosphate. Weak bases that may be mentioned further include those that, when dissolved in water and/or saliva, enable the provision (at the site of administration of compositions of the invention) of a pH of between about 7.5 and about 13.0. For the purpose of this invention, the term includes substances that are safe for use in mammals, and includes weak bases, weak base derivatives and other chemicals that convert to weak bases in vivo (e.g. precursors that convert to bases in vivo, by for example being sequentially activated in accordance with properties of the local environment). Typical pKbs of weak bases are in the range of between about −1.5 and about 16. A preferred range is between about 1 and about 10. More preferably, the weak base is safe for human consumption, for example a phosphate base, a carbonate base or a hydroxide base.

The term "water-soluble phosphate" is employed in the context of the present invention to denote a phosphate-containing inorganic salt that is capable of dissolving in water and/or saliva to form a solution. The term "water-soluble" is as defined above. Preferred phosphate salts include potassium and sodium phosphate salts, for example monosodium phosphate, more preferably disodium phosphate (e.g. disodium phosphate dihydrate) and, particularly, trisodium phosphate (e.g. trisodium phosphate anhydrous). Other bases, such as (e.g. water-soluble) carbonates, such as disodium carbonate, and hydroxides, may also be employed instead of, or in addition to, the phosphate. In such instances, all preferred features of the invention as described herein for, and all statements and/or references made in respect of, water-soluble phosphates may be applied equally to other weak bases, including carbonates, such as disodium carbonate.

It is preferred that compositions of the invention are non-effervescent. By "non-effervescent", we mean that, following intraoral administration, the components of the composition are not such (and/or are not present in such amounts) that they give rise to either:
 (a) the perceptible (i.e. the subject does not feel); or the measurable (i.e. by scientific instrumentation)
 (b) emission of bubbles of gas within saliva or other aqueous media with a pH in the range between about 4 and about 9, such as about 8.

The water-soluble phosphate material may be employed in solid state form in compositions of the invention. It is not necessary for the phosphate to be in intimate contact with the alfentanil or the weak acid or, for example, part of an interactive mixture. Surprisingly, it is not necessary for the weakly acidic material to be in contact with the phosphate base.

As mentioned previously, although it has been found that alfentanil and salts thereof are highly stable in solution, their formulation in solid state dosage forms such as those described herein has been found unexpectedly to give rise to instability problems. Further, co-formulation of alfentanil and salts thereof along with water-soluble phosphates in the solid state gives rise to further enhancement of such instability problems. This problem is solved by co-formulation with the weakly acidic material in the manner described herein.

We have found that the weak base (e.g. water-soluble phosphate) may enhance absorption of alfentanil/salt thereof across the mucosal surface. Furthermore, the chemical stability of the alfentanil/salt thereof in a composition of the invention may be improved if a small amount of weak acid (e.g. up to about 1%, such as about 0.75%, such as about 0.5%, by weight of the total weight of a composition of the invention) is employed as described herein. The presence of a weakly acid material, such as citric acid, would be expected to at least partially neutralise the absorption-enhancing effect of the weak base, but, as presented in compositions of the invention, this is not the case. Even more surprisingly, the presence of an excess of weak base, as presented in compositions of the invention, does not, as would be expected, affect the stability of the alfentanil or salt thereof.

Thus, the problem of a completely unexpected observation of instability of alfentanil and salts thereof in solid state formulations is in itself solved in a counter-intuitive way: the positive effects of the acid (provision of stability in the solid state) and the base (provision of enhanced absorption following administration) would be expected to be cancelled out by their respective negative effects (i.e. reduced absorption after administration due to the presence of acid and instability of alfentanil in the solid state due to the presence of base), but this is not observed.

According to a further aspect of the invention there is provided a method of stabilising a solid state pharmaceutical composition (e.g. a tablet for sublingual administration) comprising alfentanil or a pharmaceutically acceptable salt thereof, which method comprises providing particles of a weak acid (such as citric acid) in intimate mixture with particles of alfentanil or salt thereof. In such a method, the pharmaceutical composition may further comprise a weak base (such as a water-soluble phosphate). Such a weak base may be present in excess (by weight relative to the weak acid).

There is further provided the use of a weak acid (such as citric acid) to stabilise a solid state pharmaceutical composition (e.g. a tablet for sublingual administration) comprising alfentanil or a pharmaceutically acceptable salt thereof. Such a use preferably comprises providing particles of said weak acid in intimate mixture with particles of alfentanil or salt thereof. Preferably, the pharmaceutical composition may further comprise a weak base (such as a water-soluble phosphate), for example in excess (by weight relative to the weak acid).

Weak base, such as phosphate, and weak acid should preferably be employed to ensure that, following administration of a formulation of the invention, the pH that is achieved e.g. sublingually is weakly basic, in the range of about 7 to about 9, such as to about 8. This will depend on the nature of the phosphate (or other weak base) that is employed and suitable weight ratios that may be employed may be no less than about 1:1 (base, e.g. phosphate, to acid), such as about 2:1, for example about 4:1, such as about 10:1, e.g. no less than about 50:1. If trisodium phosphate and citric acid are employed, the ratio is preferably between about 2:1 and about 12:1, such as about 4:1.

According to a further aspect of the invention, there is provided a pharmaceutical composition comprising microparticles of alfentanil or a pharmaceutically acceptable salt thereof, particles of a weak acid (which are preferably in intimate mixture with the microparticles of alfentanil or salt thereof) and a water-soluble phosphate, wherein acid and phosphate are employed in relative amounts characterized in the composition to enables the provision (at the site of administration) of a pH of between about 7.0 and about 9.0 (such as about 8.0), preferably along with the maintenance of pH within this range for an appropriate length of time (e.g. up to about 5 minutes) to facilitate dissolution of the alfentanil microparticles, and/or absorption of alfentanil across the sublingual mucosa thereafter.

Preferred amounts of trisodium phosphate (if employed) to produce a pH in the above-stated range are about 0.25% to about 4%, such as about 2% by weight based upon the total weight of a composition of the invention. Preferred amounts of citric acid (if employed) are about 0.05% to about 1%, such as about 0.75% by weight based upon the total weight of a composition of the invention.

Compositions of the invention may also comprise disintegrant and/or superdisintegrant materials. Such materials may be presented, at least in part, as particles upon the surfaces of, and/or between, carrier particles.

The disintegrant or "disintegrating agent" that may be employed may be defined as any material that is capable of accelerating to a measurable degree the disintegration/dispersion of a composition of the invention. The disintegrant may thus provide for an in vitro disintegration time of about 30 seconds or less, as measured according to e.g. the standard United States Pharmacopeia (USP) disintegration test method (see *FDA Guidance for Industry: Orally Disintegrating Tablets*; December 2008). This may be achieved, for example, by the material being capable of swelling, wicking and/or deformation when placed in contact with water and/or mucous (e.g. saliva), thus causing tablet formulations to disintegrate when so wetted.

Suitable disintegrants (as defined in, for example, Rowe et al, *Handbook of Pharmaceutical Excipients*, 6$^{th}$ ed. (2009)) include cellulose derivatives such as hydroxypropyl cellulose (HPC), low substituted HPC, methyl cellulose, ethyl hydroxyethyl cellulose, carboxymethyl cellulose calcium, carboxymethyl cellulose sodium, microcrystalline cellulose, modified cellulose gum; starch derivatives such as moderately cross-linked starch, modified starch, hydroxylpropyl starch and pregelatinized starch; and other disintegrants such as calcium alginate, sodium alginate, alginic acid, chitosan, docusate sodium, guar gum, magnesium aluminium silicate, polacrilin potassium and polyvinylpyrrolidone. Combinations of two or more disintegrants may be used.

Preferred disintegrants include so-called "superdisintegrants" (as defined in, for example, Mohanachandran et al, *International Journal of Pharmaceutical Sciences Review and Research*, 6, 105 (2011)), such as cross-linked polyvinylpyrrolidone, sodium starch glycolate and croscarmellose sodium. Combinations of two or more superdisintegrants may be used.

Disintegrants may also be combined with superdisintegrants in compositions of the invention.

Disintegrants and/or superdisintegrants are preferably employed in an (e.g. total) amount of between 0.5 and 15% by weight based upon the total weight of a composition. A preferred range is from about 0.1 to about 5%, such as from about 0.2 to about 3% (e.g. about 0.5%, such as about 2%) by weight.

If employed in particulate form, particles of disintegrants and/or superdisintegrants may be presented with a particle size (weight and/or volume based average or mean diameter, vide supra) of between about 0.1 and about 100 µm (e.g. about 1 and about 50 µm).

Alternatively, disintegrants and/or superdisintegrants may also be present as a constituent in composite excipients. Composite excipients may be defined as co-processed excipient mixtures. Examples of composite excipients comprising superdisintegrants are Parteck® ODT, Ludipress® and Prosolv® EASYtab.

Bio/mucoadhesive materials may also be presented in compositions of the invention. Such materials may be presented upon (e.g. adhered to) the surfaces of carrier particles when components of compositions of the invention are presented in the form of interactive mixtures. Superdisintegrant materials mentioned herein may also function as bio/mucoadhesive materials.

Compositions of the invention may be employed in the treatment and/or prophylaxis of pain. Compositions of the invention are particularly useful in the treatment or prophylaxis of moderate to severe and/or short-term pain and are thus particularly useful if administered to a patient immediately before a painful diagnostic, surgical and/or care-related procedure.

By "moderate to severe" and/or "short-term" pain, we mean pain that causes a degree of discomfort and/or distraction in a patient, but which is transitory (i.e. lasts less than about an hour, such as less than about 30 minutes). When such pain is associated with a diagnostic, surgical or care-related procedure, it will normally lasts for only a short period of time (e.g. a few seconds or up to about an hour) depending upon the procedure that is performed.

Alfentanil and pharmaceutically-acceptable salts thereof may be employed in a pharmacologically effective amount, which refers to an amount of an active ingredient, which is capable of conferring a desired therapeutic effect on a treated patient, whether administered alone or in combination with another active ingredient. Such an effect may be objective (i.e. measurable by some test or marker) or subjective (i.e. the subject gives an indication of, or feels, an effect). Typically, subjective measurements of pain are conducted using numeric rating scales (NRSs) and/or visual analogue scales (VASs).

Thus, appropriate pharmacologically effective amounts of alfentanil (or salt thereof) include those that are capable of producing, and/or contributing to the production of, the desired therapeutic effect, namely prevention/abrogation of pain, including moderate to severe and/or short-term pain, for example when administered prior to a surgical, diagnostic and/or care-related procedure.

The amounts of alfentanil/salt that may be employed in compositions of the invention may thus be determined by the skilled person, in relation to what will be most suitable for an individual patient. This is likely to vary with the route of administration, the type and severity of the condition that is to be treated, as well as the age, weight, sex, renal function, hepatic function and response of the particular patient to be treated.

The total amount of alfentanil/salt thereof that may be employed in a composition of the invention may be in the range of about 0.1%, such as about 0.5%, to about 5%, such as about 2%, by weight based upon the total weight of the composition. The amount of this active ingredient may also be expressed as the amount in a unit dosage form (e.g. a tablet). In such a case, the amount of alfentanil/salt that may be present may be sufficient to provide a dose per unit dosage form that is in the range of between about 30 µg, including about 75 µg and about 3 mg (for example about 2.5 mg). A preferred range is between about 100 µg and about 2,000 µg. One, two or more dosage units may be administered concurrently.

Compositions of the invention, once prepared, may be administered as powders for sublingual administration (e.g. in the case of compositions comprising insoluble carrier particles, in the form of a spray comprising a solvent in which the alfentanil or salt thereof is not soluble or is poorly soluble). However, they are preferably directly compressed/compacted into unit dosage forms (e.g. tablets) for administration to mammalian (e.g. human) patients, for example as described hereinafter.

Compositions of the invention in the form of tablets for e.g. sublingual administration may also comprise a binder. A binder may be defined as a material that is capable of acting as a bond formation enhancer, facilitating the compression of the powder mass into coherent compacts. Suitable binders include cellulose gum and microcrystalline cellulose. If present, binder is preferably employed in an amount of between about 2% and about 20% by weight based upon the total weight of the tablet formulation. A preferred range is from about 6% to about 20%, such as from about 8% to about 17% (e.g. about 12% to about 16%) by weight.

Suitable further additives and/or excipients that may be employed in compositions of the invention, in particular those in the form of tablets for e.g. sublingual administration may comprise:

(a) lubricants (such as sodium stearyl fumarate or, preferably, magnesium stearate);

(b) flavourings (e.g. lemon, peppermint powder or, preferably, menthol), sweeteners (e.g. neohesperidin, acesulfame K or, preferably, sucralose) and dyestuffs; and/or (c) other ingredients, such as colouring agents, coating materials, preservatives and gliding agents (e.g. colloidal silica).

Compositions of the invention may be prepared by standard techniques, and using standard equipment, known to the skilled person.

When presented in the form of interactive mixtures, particles of e.g. alfentanil/salt may be dry mixed with relevant carrier particles over a period of time that is sufficiently long to enable appropriate amounts of respective active ingredients to adhere to the surface of the carrier particles. This may also apply to other active ingredients and/or any of the relevant excipients (e.g. weak acid) defined hereinbefore.

The skilled person will appreciate that, in order to obtain a formulation in the form of an interactive mixture by dry powder mixing, larger carrier particles must be able to exert enough force to break up agglomerates of smaller particles. This ability will primarily be determined by particle density, surface roughness, shape, flowability and, particularly, relative particle sizes.

Standard mixing equipment may be used in this regard. The mixing time period is likely to vary according to the equipment used, and the skilled person will have no difficulty in determining by routine experimentation a suitable mixing time for a given combination of active ingredient and carrier particle material(s).

Interactive mixtures may also be provided using techniques other than dry mixing, which techniques will be well known to those skilled in the art. For example, certain weak acids may be sprayed as an e.g. aqueous solution or suspension onto the surfaces of carrier particles in order to provide (following evaporation of the relevant solvent) particles of that material on the surfaces of such carrier particles.

Other ingredients may alternatively be incorporated by standard mixing or other formulation principles.

The compositions of the invention may be administered transmucosally, such as buccally, rectally, nasally or preferably sublingually by way of appropriate dosing means known to the skilled person. A sublingual tablet may be placed under the tongue, and the active ingredients absorbed through the surrounding mucous membranes.

In this respect, the compositions of the invention may be incorporated into various kinds of pharmaceutical preparations intended for transmucosal (e.g. sublingual) administration using standard techniques (see, for example, Lachman et al, "*The Theory and Practice of Industrial Pharmacy*", Lea & Febiger, $3^{rd}$ edition (1986) and "*Remington: The Science and Practice of Pharmacy*", Gennaro (ed.), Philadelphia College of Pharmacy & Sciences, $19^{th}$ edition (1995)).

Pharmaceutical preparations for sublingual administration may be obtained by combining compositions of the invention with conventional pharmaceutical additives and/or excipients used in the art for such preparations, and thereafter preferably directly compressed/compacted into unit dosage forms (e.g. tablets). (See, for example, *Pharmaceutical Dosage Forms: Tablets. Volume* 1, $2^{nd}$ Edition, Lieberman et al (eds.), Marcel Dekker, New York and Basel (1989) p. 354-356 and the documents cited therein.) Suitable compacting equipment includes standard tableting machines, such as the Kilian SP300, the Korsch EK0, the Korsch XP1, the Korsch XL100, the Korsch PharmaPress 800 or the Manesty Betapress.

Suitable final sublingual tablet weights are in the range of about 5 to about 300 mg, such as about 10 (e.g. about 50) to about 200 mg, for example about 30 to about 175 mg, more preferably between about 30 (e.g. about 40) and about 150 (e.g. about 140 mg). Two or more tablets may be taken simultaneously. Suitable final tablet diameters are in the range of about 3 to about 12 mm, for example about 4 to about 10 mm, and more preferably about 5 to about 9 mm. Suitable final tablet thicknesses are in the range of about 0.5 mm to about 6 mm, such as about 1.5 mm to about 3 mm. Various tablet shapes are possible (e.g. circular, triangular, square, diamond, polygon or oval).

Irrespective of the foregoing, compositions of the invention comprising disintegrants, bioadhesives (or other excipients that function by swelling) should be essentially free (e.g. less than about 20% by weight based on the total weight of the formulation) of water. It will be evident to the skilled person that "premature" hydratisation will dramatically decrease the performance of a tablet formulation in use and may result in premature dissolution of active ingredients.

Wherever the word "about" is employed herein in the context of dimensions (e.g. tablet sizes and weights, particle sizes etc.), surface coverage (e.g. of carrier particles by particles of active ingredients), amounts (e.g. relative amounts of individual constituents in a composition or a component of a composition and absolute doses (including ratios) of active ingredients and/or excipients), temperatures, pressures, times, pH values, pKa values concentrations, etc., it will be appreciated that such variables are approximate and as such may vary by ±10%, for example ±5% and preferably ±2% (e.g. ±1%) from the numbers specified herein. Wherever the word "about" is employed herein in the context of pharmacokinetic properties ($C_{max}$, $t_{max}$, AUCs), etc., it will be appreciated that such variables are approximate and as such may vary by ±15%, such as ±10%.

Compositions of the invention may be administered by way of appropriate dosing means known to the skilled person. For example, a sublingual tablet may be placed under the tongue, and the active ingredients absorbed through the surrounding mucous membrane.

Compositions of the invention may give rise to absorption characteristics for alfentanil in an entirely unexpected, and pharmaceutically useful, way. For example, compositions of the invention compared to a prior art formulation comprising fentanyl may exhibit a much faster onset of action, and/or a much higher bioavailability, being observed for compositions of the invention. This renders compositions of the invention extremely well suited to the planned indication (e.g. a short acting and fast eliminating pain relief product).

According to a further aspect of the invention, there is further provided a method of treatment of pain, such as moderate to severe and/or short-term pain, which method comprises sublingual administration to a human patient in need of such treatment of a pharmaceutical composition comprising between about 30 μg and about 3,000 μg (e.g. between about 100 μg and about 2,000 μg) of alfentanil or a pharmaceutically acceptable salt thereof, wherein said administration gives rise to a plasma concentration-time curve after said administration that possesses:

(a) $t_{max}$ (time to maximum plasma concentration) that is between about 5 (e.g. about 10) and about 25 minutes after said administration; and/or (b) a $t_{last}$ (time to last measurable plasma concentration) that is not more than about 480 minutes (e.g. about 300 minutes) after said administration; and, optionally, (c) a $C_{max}$ (maximum plasma concentration) that is between about 1 (e.g about 10) and about 100 μg per mL of plasma.

Such a method may further give rise to a plasma concentration-time curve after said administration that possesses a $C_{max}$ coefficient of variation of less than about 40%.

For a pharmaceutical composition comprising about 700 μg of alfentanil or a pharmaceutically acceptable salt thereof, such a method may further give rise to a plasma concentration-time curve after said administration, that possesses:

(a) an AUC (area under the plasma concentration-time curve) from time zero up to about 30 minutes after administration (so representing the systemic absorption during the early absorption phase) of about 150 ng·min/mL; and/or (b) an AUC from time zero up to the last concentration extrapolated to infinity based on the elimination rate constant ($AUC_{0-inf}$) of about 1,500 ng·min/mL; and/or (c) an AUC coefficient of variation of less than about 50%.

(The skilled person will appreciate that the above-mentioned AUC-related values (a) to (c) will increase/decrease proportionally if the dose of alfentanil/salt is correspondingly increased/decreased from about 700 µg.)

Further, the absolute bioavailability of alfentanil when administered sublingually in a composition of the invention may be about 70% and/or about 40% may be absorbed within the first hour.

Methods according to the invention may be employed to treat or prevent pain, particularly moderate to severe pain, which may be short acting and/or associated with a diagnostic, surgical and/or care-related procedure. In the latter case, compositions of the invention may be administered immediately before (e.g. not more than about 20 minutes, such as between about 5 and about 10 minutes, prior to) said diagnostic, surgical and/or care-related procedure.

Such methods may comprise administration of a composition of the invention as defined herein.

By "treatment" of pain, including moderate to severe and/or short-term (or short-lasting) pain, which may or may not be associated with diagnostic, surgical and/or care-related procedures), we include the therapeutic treatment, as well as the symptomatic and palliative treatment. However, by "treatment" of pain associated with a diagnostic and/or surgical procedure, we also mean the prevention or prophylaxis of the pain that would otherwise be associated with the diagnostic and/or surgical procedure.

In accordance with the invention, alfentanil or salts thereof may be combined with one or more other analgesic drugs, for example opioids, which may be administered sublingually (e.g. buprenorphine) or perorally, or other peroral analgesics (e.g. NSAIDs). Alfentanil/salts may also be combined with sedatives (e.g. benzodiazepines) or alpha 2-receptor agonists (e.g. clonidine, dexmedetomidine or ketamine). Alfentanil/salts may be combined with such other drugs either in compositions of the invention or in separate combination therapy.

The compositions of the invention are useful in the treatment of pain, such as moderate to severe and/or short-term pain, for example pain associated with painful diagnostic, surgical and/or care-related procedures.

When compositions of the invention are employed to treat or prevent pain associated with a diagnostic, surgical and/or care-related procedure, compositions are preferably administered immediately before (e.g. not more than about 20 minutes, such as between about 5 and about 10 minutes, prior to) said diagnostic or surgical procedure.

The compositions of the invention enable the production of unit dosage forms that are easy and inexpensive to manufacture, and which enable the rapid release and/or a rapid uptake of the active ingredient employed through the mucosa, such as the oral mucosa, thus enabling rapid relief of symptoms, such as those described hereinbefore.

Compositions of the invention may also have the advantage that they may be prepared using established pharmaceutical processing methods and employ materials that are approved for use in foods or pharmaceuticals or of like regulatory status.

Compositions of the invention may also have the advantage that they may be more efficacious than, be less toxic than, be shorter acting than, be more potent than, produce fewer side effects than, be more easily absorbed than, possess a better patient acceptability than, have a better pharmacokinetic profile than, and/or have other useful pharmacological, physical, or chemical properties over, pharmaceutical compositions known in the prior art, whether for use in the treatment of pain, such as moderate to severe and/or short-term pain (e.g. pain associated with diagnostic, surgical and/or care-related procedures) or otherwise.

Figure 2:
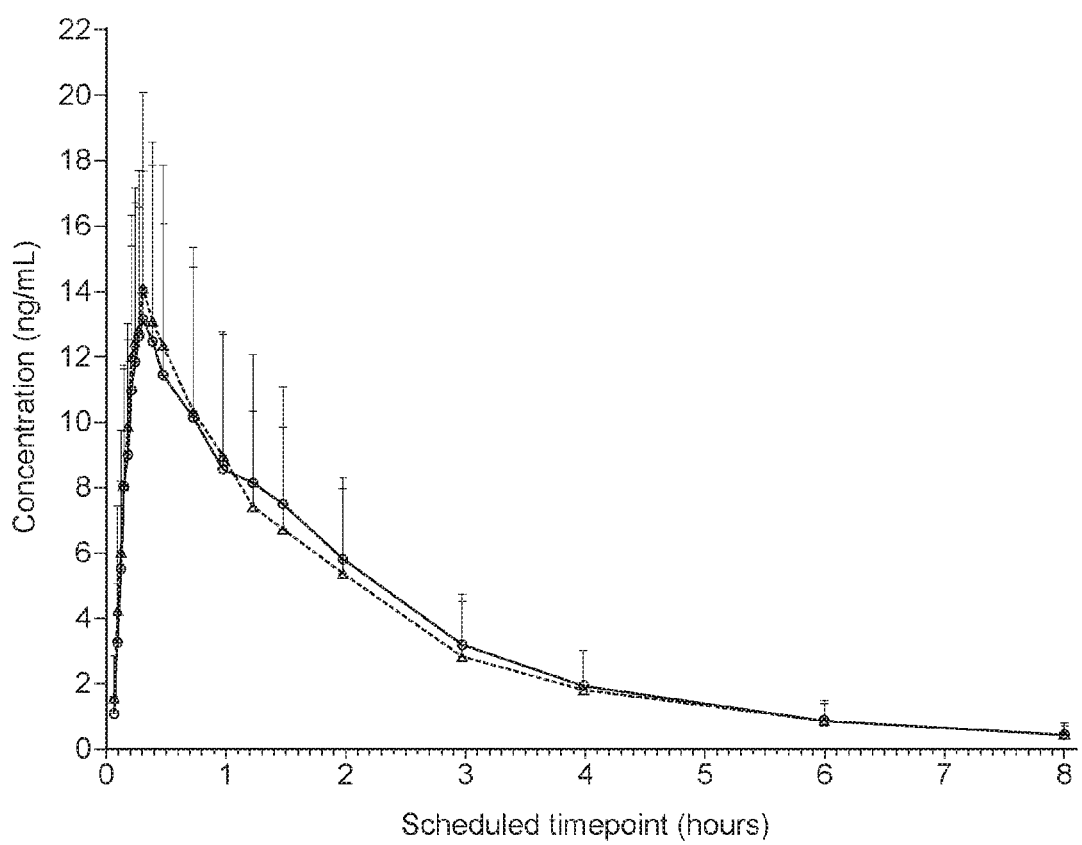
FIG. 2 shows a comparison of plasma concentration-time profiles for formulations prepared as described in Example 5 below as obtained in a clinical trial.

The invention is illustrated by way of the following examples, with reference to the attached figures, in which FIG. 1 shows a comparison of chemical stability of various batches of alfentanil-containing sublingual tablets; and FIG. 2 shows a comparison of plasma concentration-time profiles for formulations prepared as described in Example 5 below as obtained in a clinical trial.

EXAMPLE 1

Alfentanil Sublingual Tablets—Granulated Carrier Particles

Carrier Particles

Eight batches of carrier particles (employed in Tablet Batches 1 to 8 as identified in Tables 1 and 2 below) were prepared from granulated carrier particles comprising citric acid anhydrous (fine granular 16/40 grade, DSM, Switzerland, Basel) and mannitol (Pearlitol™ 400 DC, Roquette, Lestrem, France). The carrier particles were prepared as follows.

Citric acid was mortared by hand using a pestle and mortar and then sieved. The fraction with particle sizes that were between 90 µm and 180 µm was employed in the granulation. The citric acid and mannitol were firstly dry mixed in a small scale intensive mixer (Braun electronic type 4261, Braun AG, Germany) for approximately 1 minute in the following quantities:

(i) 0.2502 g citric acid and 199.8 g mannitol;
(ii) 1.2524 g citric acid and 198.8 g mannitol; and
(iii) 2.5109 g citric acid and 197.5 g mannitol.

These amounts were selected to provide citric acid contents in final tablets of 0.1%, 0.5% and 1% by weight, as appropriate.

Approximately 2.5% (w/w) water was then added over approximately 1 minute. The wet granulate was then dried in a heat cabinet for about 17 hours at 60° C. The dried granulate was then sieved. The fraction with particle sizes greater than 710 µm was removed from the final granulate.

Two further batches of carrier particles were prepared, one following the same wet granulation process but not employing any citric acid (i.e. mannitol only; 200.03 g) and a second using a dry granulation process. The first was employed to make Tablet Batch 9, and the second to make Tablet Batch 10, as identified in Tables 1 and 2 below.

Citric acid was again mortared and sieved and the fraction with particle sizes that were between 90 µm and 180 µm was employed. Citric acid (2.5492 g) and mannitol (97.48 g) were dry mixed in a tumble blender (Turbula, type T2F, WAG, Switzerland) for 15 minutes). These amounts were selected to provide a citric acid content in final tablets of 2% by weight.

Magnesium stearate (vegetable origins; 0.44 g; Peter Greven, Münstereifel, Germany; sieved through a sieve with a size of 0.5 mm) was then added to 88.52 g of the mannitol/citric acid mixture and the blending continued for 2 minutes. The powder was compressed into briquettes using a single punch press (Korsch EK-0) equipped with 20 mm round, flat faced, punches, to give briquettes with a width of approximately 1.9 mm and a crushing strength of 90 N. The briquettes were then ground, firstly though a sieve with a size of 1,560 μm and then through another sieve of a size 710 μm. The fraction of a size greater than 710 μm was discarded.

Granulated carrier (amounts presented in Table 1 below) comprising one of the above carrier particle blends was mixed together with micronized alfentanil hydrochloride (amounts presented in Table 1 below; Johnson Matthey, West Deptford, N.J., US; volume based mean particle size (diameter) 2.360 μm) in a tumble blender (Turbula mixer, type T2F, WAG, Switzerland) with a 100 mL DUMA container for 20 hours at 75 rpm.

The resultant interactive mixture was than mixed together with microcrystalline cellulose (3.35 g; Prosolv™ SMCC 90 (particle size specification limits: d(10)—25-46 μm, d(50)—98-146 μm, d(90)—195-276 μm; JRS Pharma, Rosenberg, Germany]), croscarmellose sodium (0.261 g; AcDiSol™, FMC Biopolymer, Cork, Ireland; approximate particle size around 50 μm) and trisodium phosphate anhydrous (fine granules; 0.75 g or 1 g, in appropriate amounts to provide 3% or 4%, respectively in the final tablet; Budenheim, Germany) in the tumble blender for a further 30 minutes.

Magnesium stearate (0.125 g; sieved through a sieve with a size of 0.5 mm) was then added to this mixture and mixing continued in the tumble blender for a further 2 minutes.

The final powder mixture was then compressed into tablets using a single punch press (Korsch EK-0) equipped with 6 mm round, flat faced, bevelled-edged punches, to give tablets with a final tablet weight of 70 mg and a tablet crushing strength of 20 N.

Different batches of tablets were prepared as described in Table 1 below.

TABLE 1

| Batch | Alfentanil dose (μg) | Alfentanil HCl amount (g) | Mannitol amount (g) | Citric acid amount (g) | Trisodium phosphate amount (g) |
| --- | --- | --- | --- | --- | --- |
| 1 | 350 | 0.141 | 20.11 | 0.025 | 1 |
| 2 | 700 | 0.281 | 19.97 | 0.025 | 1 |
| 3 | 350 | 0.141 | 20.01 | 0.125 | 1 |
| 4 | 350 | 0.141 | 20.26 | 0.125 | 0.75 |
| 5 | 700 | 0.281 | 19.87 | 0.125 | 1 |
| 6 | 700 | 0.281 | 20.12 | 0.125 | 0.75 |
| 7 | 350 | 0.141 | 19.89 | 0.25 | 1 |
| 8 | 700 | 0.281 | 19.74 | 0.25 | 1 |
| 9 | 350 | 0.141 | 20.14 | 0 | 1 |
| 10 | 350 | 0.141 | 19.64 | 0.5 | 1 |

Stability studies were performed. Samples were subjected to the following storage conditions +25° C./60% RH, and +40° C./75% RH, with analysis conducted at 3 months.

50 tablets of each batch were packed as a bulk in 30 mL DUMA container and and subjected to the following storage conditions +25° C./60% RH and +40° C./75% RH (following ICH requirements of ±2° C. and 5% RH). At 1 and 3 months 10 tablets were removed from each DUMA container and analysed for organic impurities.

Impurities resulting from degradation of alfentanil were determined using HPLC analysis and UV detection at 220 nm. The principle alfentanil-derived degradation products had previously been identified as N-phenylpropanamide, N-oxides (cis/trans) of alfentanil, and corresponding dehydrated N-oxides.

The tablets were dissolved in ammonium acetate buffer and acetonitrile and analysed on a C18 column (2.1×150 mm, Waters Xterra) using a gradient mobile phase system containing acetonitrile and ammonium acetate buffer. Related substances were quantified as Area % of the total area of peaks corresponding to alfentanil (all non-alfentanil peaks with Area % s that were greater than 0.05% were included).

Table 2 below shows a comparison of various batches after storage in long term. The total amount of alfentanil-derived impurities is presented as Area %.

TABLE 2

| Batch | Dose API (μg) | Amount Citric Acid (%) | Amount of Phosphate (%) | Total Impurities (Area %) 25/60 | Total Impurities (%) 40/75 |
| --- | --- | --- | --- | --- | --- |
| 1 | 350 | 0.1 | 4 | 0.07 | 0.90 |
| 2 | 700 | 0.1 | 4 | 0.07 | 0.24 |
| 3 | 350 | 0.5 | 4 | 0.06 | 0.28 |
| 4 | 350 | 0.5 | 3 | 0.06 | 0.39 |
| 5 | 700 | 0.5 | 4 | 0.06 | 0.21 |
| 6 | 700 | 0.5 | 3 | 0.06 | 0.18 |
| 7 | 350 | 1.0 | 4 | 0.07 | 0.06 |
| 8 | 700 | 1.0 | 4 | 0.06 | 0.07 |
| 9 | 350 | 0 | 4 | 0.11 | 1.67 |
| 10 | 350 | 2.0 | 4 | 0.15 | 0.15 |

Results after storage show a clear difference in the amount of impurities generated between the batch with no citric acid (Batch 9) and the other batches. The differences between the other batches are very small.

EXAMPLE 2

Alfentanil Sublingual Tablets

EXAMPLE 2.1—GRANULATED CARRIER PARTICLE BATCHES

Granulated carrier particles comprising citric acid anhydrous (fine granular 16/40 grade, DSM, Switzerland, Basel) or trisodium citrate dihydrate (Citrique Belge, Belgium) and mannitol (Pearlitol™ 400 DC, Roquette, Lestrem, France) were prepared as follows.

Citric acid and sodium citrate were first milled using an air jet mill (Pilotmill-1; Food and Pharma Systems, Italy). Citric acid was milled to volume-based particle sizes (D(4, 3)) of 4.3 μm and 99 μm, and sodium citrate was milled to particle sizes of 9.6 μm, 21 μm and 94 μm.

The citric acid/citrate and mannitol were firstly dry mixed in a small scale intensive mixer (Braun electronic type 4261, Braun AG, Germany) for approximately 1 minute in the following quantities:
 (i) 0.125 g citric acid/citrate and 99.875 g mannitol for a 100 g batch (or 0.25 g citric acid and 199.75 g mannitol for a 200 g batch); and
 (ii) 2.502 g citric acid and 97.498 g mannitol for a 100 g batch (or 5.004 g citric acid and 194.996 g mannitol for a 200 g batch).
These amounts were selected to provide citric acid contents in final tablets of 0.1% and 2.0% by weight, as appropriate.

Approximately 2.5% (w/w) water was then added over approximately 30 seconds. The wet granulate was then dried in a heat cabinet for about 20 hours at 60° C. The dried granulate was then seived. The fraction with particle sizes greater than 710 µm was removed from the final granulate.

Granulated carrier (20.10 g) was mixed together with micronized alfentanil hydrochloride (0.141 g; Johnson Matthey, West Deptford, N.J., US; volume based mean particle size diameter 2.360 µm) in a tumble blender (Turbula mixer, type T2F, WAG, Switzerland) with a 100 mL Duma container for 20 hours at 72 rpm.

The resultant interactive mixture was than mixed together with microcrystalline cellulose (3.33 g), croscarmellose sodium (0.361 g) and trisodium phosphate anhydrate anhydrous (1.06 g) or disodium phosphate dihydrate (Merck KGaA, Darmstadt, Germany; 1.06 g) in the tumble blender for a further 30 minutes.

Magnesium stearate (0.125 g; sieved through a sieve with a size of 0.5 mm) was then added to this mixture and mixing continued in the tumble blender for a further 2 minutes.

The final powder mixture was then compressed into tablets using a single punch press (Korsch EK-0) equipped with 6 mm round, flat faced, bevelled-edged punches, to give tablets with a final tablet weight of 70 mg and a tablet crushing strength of 20 N.

Batches of tablets were prepared as follows:
(1) citric acid (2%; D(4,3): 4.3 µm); disodium phosphate dihydrate
(2) citric acid (2%; D(4,3): 99 µm); disodium phosphate dihydrate
(3) sodium citrate (0.1%; D(4,3): 94 µm); disodium phosphate dihydrate
(4) sodium citrate (0.1%; D(4,3): 9.6 µm); trisodium phosphate anhydrous
(5) sodium citrate (2%; D(4,3): 9.6 µm); trisodium phosphate anhydrous

EXAMPLE 2.2—INTERACTIVE MIXTURE BATCHES

Essentially the same procedure as that described in Example 2.1(b) was carried out to prepare further batches of tablets with non-granulated carrier particles, but in which, instead, citric acid or sodium citrate is presented on the surfaces of mannitol carrier particles.

Mannitol (19.6 g, 19.8 g or 20.1 g depending upon how much citric acid or citrate was employed) was mixed together with micronized alfentanil hydrochloride (0.141 g) and citric acid or sodium citrate of different particle size distributions (0.025 g, 0.25 g or 0.5 g as appropriate, to provide 0.1%, 0.5% and 2%, respectively of citric acid/citrate in the final tablets), in a tumble blender for 20 hours at 72 rpm.

The resultant interactive mixture was then mixed together with microcrystalline cellulose (3.33 g), croscarmellose sodium (0.361 g) and trisodium phosphate anhydrous or disodium phosphate dihydrate (1.06 g) for a further 30 minutes.

Magnesium stearate (0.125 g; sieved through a sieve with a size of 0.5 mm) was then added to this mixture and mixing continued for a further 2 minutes.

The final powder mixtures were then compressed into tablets as described in Example 2.1 above to produce batches of tablets as follows:

(6) sodium citrate (2%; D(4,3): 9.6 µm); disodium phosphate dihydrate
(7) sodium citrate (0.1%; D(4,3): 94 µm); disodium phosphate dihydrate
(8) sodium citrate (2%; D(4,3): 9.6 µm); disodium phosphate dihydrate
(9) citric acid (0.1%; D(4,3): 4.3 µm); trisodium phosphate anhydrous
(10) citric acid (2%; D(4,3): 99 µm); trisodium phosphate anhydrous
(11) sodium citrate (1%; D(4,3): 21 µm); trisodium phosphate anhydrous
(12) sodium citrate (1%; D(4,3): 21 µm); trisodium phosphate anhydrous

EXAMPLE 2.3 (COMPARATIVE)—BULK BATCHES

Essentially the same procedure as that described in Example 2.2 was carried out to prepare a further batch of tablets with citric acid or sodium citrate presented as part of the bulk (i.e. not presented on the surfaces of mannitol carrier particles).

Mannitol (19.6 g, 19.8 g or 20.1 g depending upon how much citric acid or citrate was employed) was mixed together with micronized alfentanil hydrochloride (0.141 g) in the tumble blender for 20 hours at 72 rpm.

The resultant interactive mixture was than mixed together with citric acid or sodium citrate of different particle size distributions (0.025 g, 0.25 g or 0.5 g as appropriate, to provide 0.1%, 0.5% and 2%, respectively of citric acid/citrate in the final tablets), microcrystalline cellulose (3.33 g), croscarmellose sodium (0.361 g) and trisodium phosphate anhydrous or disodium phosphate dihydrate (1.06 g) for a further 30 minutes.

Magnesium stearate (0.125 g; sieved through a sieve with a size of 0.5 mm) was then added to this mixture and mixing continued for a further 2 minutes.

The final powder mixtures were then compressed into tablets as described in Example 2.1 above to produce batches of tablets as follows:
(13) citric acid (0.1%; D(4,3): 4.3 µm); disodium phosphate dihydrate
(14) citric acid (0.1%; D(4,3): 99 µm); disodium phosphate dihydrate
(15) sodium citrate (2%; D(4,3): 94 µm); trisodium phosphate anhydrous
(16) sodium citrate (1%; D(4,3): 21 µm); trisodium phosphate anhydrous
(17) sodium citrate (1%; D(4,3): 21 µm); trisodium phosphate anhydrous
(18) sodium citrate (1%; D(4,3): 21 µm); trisodium phosphate anhydrous
(19) sodium citrate (2%; D(4,3): 9.6 µm); disodium phosphate dihydrate

EXAMPLE 2.4—STABILITY STUDIES

Stability studies were performed on Batches 1 to 19 above. Samples were subjected to +40° C./75% RH, with analysis conducted at 4 weeks.

Analysis was carried out substantially as described in Example 1 above.

Table 3 below shows a comparison of various batches after 4 weeks. The total amount of alfentanil-derived impurities is presented as Area %.

TABLE 3

| Batch No. | Acid/Salt | Mixing Mode | Impurities (Area %) |
|---|---|---|---|
| 13 | acid | bulk | 0.85 |
| 14 | acid | bulk | 1.4 |
| 2 | acid | granule | 0.07 |
| 1 | acid | granule | 0.06 |
| 9 | acid | interactive | 0.53 |
| 10 | acid | interactive | 0.69 |
| 15 | salt | bulk | 1.6 |
| 16 | salt | bulk | 1.7 |
| 17 | salt | bulk | 1.9 |
| 18 | salt | bulk | 1.9 |
| 19 | salt | bulk | 1.6 |
| 3 | salt | granule | 0.57 |
| 4 | salt | granule | 0.28 |
| 5 | salt | granule | 0.22 |
| 6 | salt | interactive | 1.7 |
| 7 | salt | interactive | 1.8 |
| 8 | salt | interactive | 1.1 |
| 11 | salt | interactive | 1.7 |
| 12 | salt | interactive | 1.5 |

The results are also presented in FIG. 1. Although is a clear trend that intimate mixing of both citric acid or citrate with alfentanil gives better stability (with bulk mixing giving rise to most impurities), the effect is more pronounced with citric acid.

EXAMPLE 3

Alfentanil Sublingual Tablets

Tablets comprising a 700 µg dose of alfentanil hydrochloride were prepared in accordance with the procedure described in Example 1 as follows:

(a) Citric acid was mortared and sieved. The fraction with particle sizes that were less than 180 µm was employed in the granulation. The citric acid (7.5 g) and mannitol (592.5 g) were dry mixed in a small scale intensive mixer (Philips HR 775, Philips, Netherlands). The amounts were selected to provide a citric acid content in final tablets of 1% by weight.

Approximately 2.5% (w/w) water was then added over approximately 2 minutes, with a further 1 minute of additional massing time. The wet granulate was then dried in a heat cabinet for about 20 hours at 60° C. The dried granulate was then seived. The fraction with particle sizes greater than 710 µm was removed from the final granulate.

(b) Granulated carrier (279.9 g) was mixed together with micronized alfentanil hydrochloride (3.935 g; Johnson Matthey, West Deptford, N.J., US; volume based mean particle size diameter 2.360 µm) in a tumble mixer (Turbula mixer, type I-57EQ, WAG, Switzerland) with a 1 L stainless steel container for 20 hours at 47 rpm.

The resultant interactive mixture was than mixed together with microcrystalline cellulose (46.75 g), croscarmellose sodium (3.65 g) and trisodium phosphate anhydrous (14.0 g, Budenheim, Germany) in the tumble blender for a further 30 minutes.

Magnesium stearate (1.75 g; sieved through a sieve with a size of 0.5 mm) was then added to this mixture and mixing continued in the tumble blender for a further 2 minutes.

The final powder mixture was then compressed into tablets using a single punch press (Korsch XP1 I-236EQ) equipped with 6 mm round, flat faced, bevelled-edged punches, to give tablets with a final tablet weight of 70 mg and a tablet crushing strength of 20 N.

EXAMPLE 4

Stability Study Comparison

Stability studies were carried out on various batches of two different alfentanil-containing formulations:

(a) sublingual 700 µg alfentanil tablets (prepared essentially according to the methodology described in Example 3 above except that no granulation step (a) was performed with citric acid (i.e. only mannitol was employed in the carrier particles), and no phosphate base was added along with the microcrystalline cellulose and the croscarmellose sodium); and (b) sublingual 700 µg alfentanil tablets (prepared essentially according to the methodology described in Example 3 above)

Samples were subjected to various conditions as set out in Table 4 below, with analysis carried out substantially as described in Example 1 above (with tablets packaged in aluminium sachets; 42 tablets/sachet). Table 4 below shows a comparison for various batches of tablets ((a) and (b)) after 6 months. The total amount of alfentanil-derived impurities is presented as Area % (where ND means no impurities detected).

TABLE 4

| Formulation | Batch | Storage condition | Total peaks |
|---|---|---|---|
| (a) | (a1) | 25° C./60% RH | ND |
| (a) | (a2) | 40° C./75% RH | 1.73 |
| (a) | (a3) | 25° C./60% RH | 0.12 |
| (a) | (a4) | 40° C./75% RH | 2.05 |
| (b) | (a1) | 25° C./60% RH | ND |
| (b) | (a2) | 40° C./75% RH | ND |
| (b) | (a3) | 25° C./60% RH | ND |
| (b) | (a4) | 40° C./75% RH | ND |

EXAMPLE 5

Randomised, Open, Cross-Over Study to Assess the Pharmacokinetics of Sublingual Alfentanil Tablet Formulations in Healthy Subjects Study Design An open label, randomised, two-way crossover Phase I study was conducted at the Karolinska Trial Alliance (KTA), Phase I Unit, Karolinska Universitetssjukhuset, Huddinge, M62, 141 86 Stockholm, Sweden between January and February 2012.

The primary objective of the study was to evaluate the pharmacokinetics (PK) after administration of two different sublingual alfentanil-containing tablet formulations in single doses in twelve healthy, unblocked (i.e. without opioid antagonist(s) having been administered to subjects), male and female subjects. Secondary objectives included assessment of safety, tolerability, taste and acceptability of the formulations.

Subjects attended a screening visit within 28 days prior to Day −1. Following screening, subjects were admitted to the Phase I Unit on the morning of Day −1 and remained resident until approximately 24 hours post-last dose for completion of study procedures and PK blood sampling on Day 3, after which they were discharged.

To avoid any carry-over effects between treatments, the different treatments were administered at least 24 hours apart (Days 1 to 2), corresponding to a washout period of 16 half-lives (the half-life of alfentanil is approximately 1.5 hours).

Main inclusion criteria were that the male or female subjects were healthy, unblocked, aged between 18 and 45 years (inclusive), with a body mass index (BMI) between 18.5 and 29.0 kg/m² (inclusive), and a weight within 50.0 to 100.0 kg.

Approximately the same number of each gender was randomised into the study. The following treatments were given to each subject according to a randomised treatment sequence:

(I) sublingual 700 µg alfentanil tablets (a); and
(II) sublingual 700 µg alfentanil tablets (b), both prepared essentially according to the methodology described in Example 4 above.

Each subject participated in the study for approximately 6 weeks, from screening until follow-up. In treatments (I) and (II), formulations (a) and (b), respectively, were administered in single doses with a washout period of 24 hours between treatments. After completion of the study period, all subjects participated in an end of study visit (Visit 3), 3 to 8 days after the last dose.

Primary PK Parameters

If data permitted, the following PK parameters for both sublingual tablet formulations were calculated:

$C_{max}$ (maximum plasma concentration).
$t_{max}$ (time to maximum plasma concentration).
$AUC_{0-last}$ (area under the plasma drug concentration-time curve from time zero to the time of the last quantifiable plasma concentration).
$AUC_{inf}$ (area under the plasma drug concentration-time curve from time zero to infinity).
$F_{rel}$ (relative bioavailability).

Secondary PK Parameters $t_{lag}$ (time immediately prior to first quantifiable concentration following sublingual administration).
$t_{first}$ (time to first quantifiable concentration).
$t_{1/2}$ (terminal half-life).
$\lambda_z$ (terminal elimination rate constant).
CL/F (apparent clearance following sublingual administration).
V/F (apparent volume of distribution following sublingual administration).
$AUC_{extr}$ (% AUC extrapolated from $C_{last}$ to infinity).

Safety and Tolerability Variables

Safety was assessed by adverse events (AEs), laboratory safety assessments (haematology, biochemistry and urinalysis), 12-lead electrocardiogram (ECG), respiration rate, blood pressure (BP), pulse, body temperature and pulse oximetry (to measure arterial oxygen saturation).

Tolerability was assessed by visual review of the sublingual mucosa by an appropriately experienced physician. A questionnaire was used to ask the subjects about taste and acceptability of the sublingual formulations.

Statistical Methods

The relative bioavailability of formulation (b) relative to formulation (a) was assessed, based on the primary PK parameters $C_{max}$, $AUC_{0-last}$, and $AUC_{inf}$. These were $\log_e$-transformed prior to the statistical analysis and compared using a mixed effects ANOVA model as follows:

$\text{Log}_e(\text{parameters})=\text{Treatment}+\text{Period}+\text{Sequence}+\text{Subject(Sequence)}+\text{Error}$ Treatment, period and sequence were included as fixed effects and subject within sequence as a random effect in the model. Formulation (a), which is not according to the invention, was considered the reference treatment. Differences in the least squares means (LSmeans) between the two treatments and associated 90% confidence intervals were determined. Back-transformation provided a point estimate (geometric mean ratio of test to reference treatment) and conventional 90% confidence intervals.

The safety population and the population for taste and acceptability assessments included all subjects who had received at least one dose of investigational medicinal product (IMP).

Summary tables and listings were provided for the safety and tolerability (local tolerability, and taste and acceptability questionnaire) assessments. In general, descriptive data summaries of continuous outcomes included number of subjects with observations (n), mean, standard deviation (SD), median, minimum, maximum and coefficient of variation (CV %). CV % was not presented for change from baseline data. Categorical outcomes were summarized by number and percent of subjects.

Results and Conclusions

After sublingual administration, alfentanil concentrations rapidly increased and were maximal by around 20 and 18 minutes for both formulations (a) and (b), respectively. In many instances, a secondary peak was apparent after both formulations were administered. Concentrations then declined in a monophasic manner, and were predominantly below the limit of quantification after 8 hours post-dose for both formulations.

Systemic exposure to alfentanil, in terms of mean $C_{max}$, $AUC_{0-last}$ and $AUC_{inf}$ was comparable for both formulations. For both formulations, the percentage of $AUC_{inf}$ that was extrapolated was less than 9%.

The median $t_{lag}$ for alfentanil for both formulations was 0.0333 hours (2 minutes), with quantifiable concentrations being achieved by 0.100 hours (6 minutes) in all subjects. Maximal concentrations were attained at median times of 0.33 and 0.30 hours (20 and 18 minutes) for formulation (a) and formulation (b), respectively.

For $C_{max}$, $AUC_{0-last}$ and $AUC_{inf}$ the bioavailability of formulation (b) relative to formulation (a) was close to 100% and the confidence intervals around the ratios were fully contained within the bioequivalence limits of 0.8-1.25.

Both t % and CL/F were comparable for the two formulations, with respective means of 1.3 hours and 31 L/h for formulation (a), and 1.2 hours and 32 L/h for formulation (b). The mean V/F was slightly lower for formulation (b) compared to formulation (a) with respective means of 46 L and 54 L.

In general, the number and frequency of treatment-emergent AEs (TEAEs) was similar after subjects had taken both formulations (10 subjects [90.9%] experiencing 25 TEAEs after treatment with formulation (a) and 11 subjects [91.7%] experiencing 30 TEAEs after treatment with formulation (b)).

The most frequent TEAE by preferred term after both formulations was somnolence. Other common TEAEs reported were: sedation, headache and feeling hot.

The majority of TEAEs were mild or moderate. Only one subject experienced any severe TEAEs. Subject R005 experienced TEAEs of severe headache and presyncope after treatment with formulation (a).

One subject experienced a TEAE that led to discontinuation from the study. Subject R008 experienced the TEAE of influenza like symptoms after treatment with formulation (b), which was assessed as not related. As a result of this TEAE, the subject discontinued from the study before receiving formulation (a).

Two clinically significant physical abnormalities were observed at follow-up. One subject experienced a worsening of atopic dermatitis, which was assessed as unlikely to be related to study treatment, between screening and follow-up. Another subject presented with pharyngeal erythema at follow-up.

There was a slight trend towards a decrease in mean BP shortly after treatment with both formulations (a) and (b). Two subjects experienced clinically significant decreases in BP. No other vital signs had clinically significant changes and all vital signs returned to baseline values by 4 hours post treatment with both formulations. Overall, no trends in abnormal laboratory parameters were identified. Values that occurred outside the reference limits at the follow-up visit were reported infrequently for all haematology and biochemistry parameters (by 2 subjects), as well as for urinalysis parameters (by 3 subjects). No laboratory values outside the reference limits were assessed as clinically significant.

Both formulations were well tolerated and the taste of both was considered acceptable by the majority of subjects. All subjects said that they would use both formulations if available commercially. A comparison between the two mean plasma concentration-time profiles is presented in FIG. 2 (circles—formulation (a); triangles—formulation (b)).

There were no findings in the study that raised any safety concerns.

EXAMPLE 6

Alfentanil Sublingual Tablets

Tablets comprising 700 µg and 350 µg of alfentanil hydrochloride were prepared as follows.

Citric acid (anhydrous) was milled using an air jet mill (Pilotmill.1; Food and Pharma System, Italy). Mannitol (Pearlitol 400 DC) was pre-mixed together with different amounts of micronized citric acid in a tumble blender for 2 to 3 hours. Micronised alfentanil hydrochloride was added to the mixture and mixed for another 20 hours.

The resultant interactive mixture was then mixed together with microcrystalline cellulose (Prosolv SMCC 90), croscarmellose sodium (Ac-Di-Sol) and trisodium phosphate anhydrous or disodium carbonate anhydrous for further 30 minutes.

Magnesium stearate (sieved through a sieve with a size of 0.5 mm) was added to the mixture and mixing continued for further 2 minutes.

The final powder mixtures were then compressed into tablets using a single punch press (Korsch EK-0) equipped with 7 mm round, flat faced, beveled-edged punches, to give tablets with a final tablet weight of 105 mg and a tablet crushing strength of 30 N. The relative percentage amounts of the various ingredients above in 105 mg tablets for the various batches is shown in Table 5 below.

TABLE 5

| Batch | 1 | 2 | 3 | 4 | 5 | 6 |
|---|---|---|---|---|---|---|
| Alfentanil hydrochloride | 0.750[1] | 0.750[1] | 0.380[2] | 0.380[2] | 0.380[2] | 0.380[2] |
| Mannitol | 82.75 | 82.95 | 83.32 | 83.42 | 83.85 | 83.65 |
| Citric acid | 0.40 | 0.20 | 0.20 | 0.10 | 0.20 | 0.40 |
| Trisodium phosphate | 1.20 | 1.20 | 1.20 | 1.20 | — | — |
| Disodium carbonate | — | — | — | — | 0.67 | 0.67 |
| Silicified microcrystalline cellulose | 13.4 | 13.4 | 13.4 | 13.4 | 13.4 | 13.4 |
| Croscarmellose sodium | 1.00 | 1.00 | 1.00 | 1.00 | 1.00 | 1.00 |
| Magnesium stearate | 0.50 | 0.50 | 0.50 | 0.50 | 0.50 | 0.50 |

[1]Corresponds to 700 µg alfentanil base
[2]Corresponds to 350 µg alfentanil base

EXAMPLE 7

Stability Study

Stability studies were carried out on tablets from the six batches of Example 6 above.

Samples were subjected to +40° C./75% RH with analysis conducted at 3 months. 26 or 36 tablets of each batch were packed in aluminium sachets. Impurities resulting from degradation of alfentanil were determined using HPLC as described in Example 1 above.

Table 6 below shows a comparison for various batches of tablets. The total amount of alfentanil-derived impurities is presented as Area %.

TABLE 6

| Batch | 1 | 2 | 3 | 4 | 5 | 6 |
|---|---|---|---|---|---|---|
| Total impurities | 0.11 | 0.15 | 0.19 | 0.21 | 0.20 | 0.14 |

In addition, disintegration times for tablets prepared from the above batches (either 3 or 6 tablets in total for each batch) were determined by a standard US Pharmacopeia method (USP35/NF30 <701>) immediately after preparation (0 months) and three months after storage (3 months) under the above conditions. The results for the tablet with the longest disintegration time (in seconds) in each batch are presented in Table 7 below.

TABLE 7

| Batch | 1 | 2 | 3 | 4 | 5 | 6 |
|---|---|---|---|---|---|---|
| 0 months | 14 | 14 | 14 | 15 | 16 | 16 |
| 3 months | 11 | 15 | 10 | 13 | 18 | 16 |

All tablet batches were acceptable from a stability and disintegration time point of view. The batches containing disodium carbonate were non-effervescent.

The invention claimed is:
1. A pharmaceutical composition suitable for sublingual delivery which comprises a mixture comprising:
   (a) microparticles of alfentanil, or a pharmaceutically acceptable salt thereof, which microparticles are attached to, adhered to or associated with the surfaces of larger carrier particles, which carrier particles comprise a composite of:
      (i) a weak acid material; and
      (ii) another carrier particle material; and
   (b) a weak base.

2. A composition as claimed in claim 1, wherein the acid is citric acid.

3. A composition as claimed in claim 1, wherein the weak base comprises a phosphate.

4. A composition as claimed in claim 1, wherein the other carrier particle material is mannitol.

5. A pharmaceutical composition as claimed in claim 1, which further comprises a disintegrant.

6. A composition as claimed in claim 5, wherein the disintegrant is a superdisintegrant selected from croscarmellose sodium, sodium starch glycolate, crosslinked polyvinylpyrrolidone or a mixture thereof.

7. A composition as claimed in claim 1 which is in the form of a tablet suitable for sublingual administration.

8. A process for the preparation of a composition of claim 1, which comprises dry mixing carrier particles with alfentanil or salt thereof.

9. A process for the preparation of a sublingual tablet of claim 1, which comprises directly compressing or compacting said composition.

10. A method of treatment of pain, which method comprises administration of a composition of claim 1 to a person suffering from, or susceptible to pain.

11. A composition of claim 1 for use in a method of treatment of pain.

12. A method as claimed in claim 10, wherein the pain is moderate to severe pain.

13. A composition as claimed in claim 11, wherein the pain is moderate to severe pain.

14. A method as claimed in claim 12, wherein the treatment is short term.

15. A composition as claimed in claim 13, wherein the treatment is short term.

16. A method as claimed in claim 12, wherein the pain is associated with a diagnostic, a surgical or a care-related procedure.

17. A composition as claimed in claim 13, wherein the pain is associated with a diagnostic, a surgical or a care-related procedure.

18. A method as claimed in claim 12, wherein the composition is administered not more than about 20 minutes prior to a diagnostic, a surgical, or a care-related procedure.

19. A composition as claimed in claim 13 wherein the composition is administered not more than about 20 minutes prior to a diagnostic, a surgical, or a care-related procedure.

20. A method of treatment of pain as claimed in claim 10, which method comprises sublingual administration to a human patient in need of treatment of a pharmaceutical composition comprising between about 30 μg and about 3,000 μg of alfentanil or a pharmaceutically acceptable salt thereof, wherein said administration gives rise to a plasma concentration-time curve after said administration that possesses:
 (I) a $t_{max}$ (time to maximum plasma concentration) that is between about 10 and about 25 minutes after said administration; and/or
 (II) a $t_{last}$ (time to last measurable plasma concentration) that is not more than about 300 minutes after said administration; and, optionally,
 (III) a $C_{max}$ (maximum plasma concentration) that is between about 10 and about 100 ng per mL of plasma.

21. A method as claimed in claim 20 which comprises administration of a pharmaceutical composition suitable for sublingual delivery which comprises a mixture comprising:
 (a) microparticles of alfentanil, or a pharmaceutically acceptable salt thereof, which microparticles are presented on the surfaces of larger carrier particles;
 (b) a water-soluble weak base; and
 (c) a compound which is a weak acid, which acid is presented in intimate mixture with the microparticles of alfentanil or salt thereof.

22. The composition of claim 3, wherein said phosphate is trisodium phosphate.

* * * * *